United States Patent [19]

Ingle, Jr.

[11] 4,326,405
[45] Apr. 27, 1982

[54] APPARATUS FOR DETECTING BONDING DEFECTS IN LAMINATES

[76] Inventor: Harold R. Ingle, Jr., 2665 Jamerson Rd., NE., Marietta, Ga. 30066

[21] Appl. No.: 176,935

[22] Filed: Aug. 11, 1980

[51] Int. Cl.³ .......................................... G01N 29/00
[52] U.S. Cl. .................................................. 73/37
[58] Field of Search ............... 73/37, 150 A, 827, 37.7

[56] References Cited

U.S. PATENT DOCUMENTS

| | | | |
|---|---|---|---|
| 2,901,906 | 9/1959 | Emmons | 73/37 |
| 3,460,375 | 8/1969 | Auger | 73/37 |
| 4,043,179 | 8/1977 | Ingle, Jr. | 73/37 |

Primary Examiner—Jerry W. Myracle
Attorney, Agent, or Firm—Seidel, Gonda, Goldhammer & Panitch

[57] ABSTRACT

An apparatus is provided for testing of bonded laminates which include a substrate and a face sheet bonded thereto. The apparatus has at least one air nozzle arranged to direct high velocity air in a direction generally radially outward of the circular pattern at a shallow angle to the face sheet of the laminate. A detection plate on the examining surface of the device is encircled by the air nozzles. The detection plate has associated therewith means for detecting when the face sheet of the laminate is deflected toward the detection plate, indicating that the laminate is not bonded to the substrate in that area. High pressure air is introduced through the air nozzles thereby producing an air cushion between the examining surface of the apparatus and the face sheet of the laminate and simultaneously producing a vacuum in the area between the detection plate and the face sheet, whereby the face sheet will be deflected toward the detection plate in an area where the face sheet is not bonded to the substrate.

17 Claims, 8 Drawing Figures

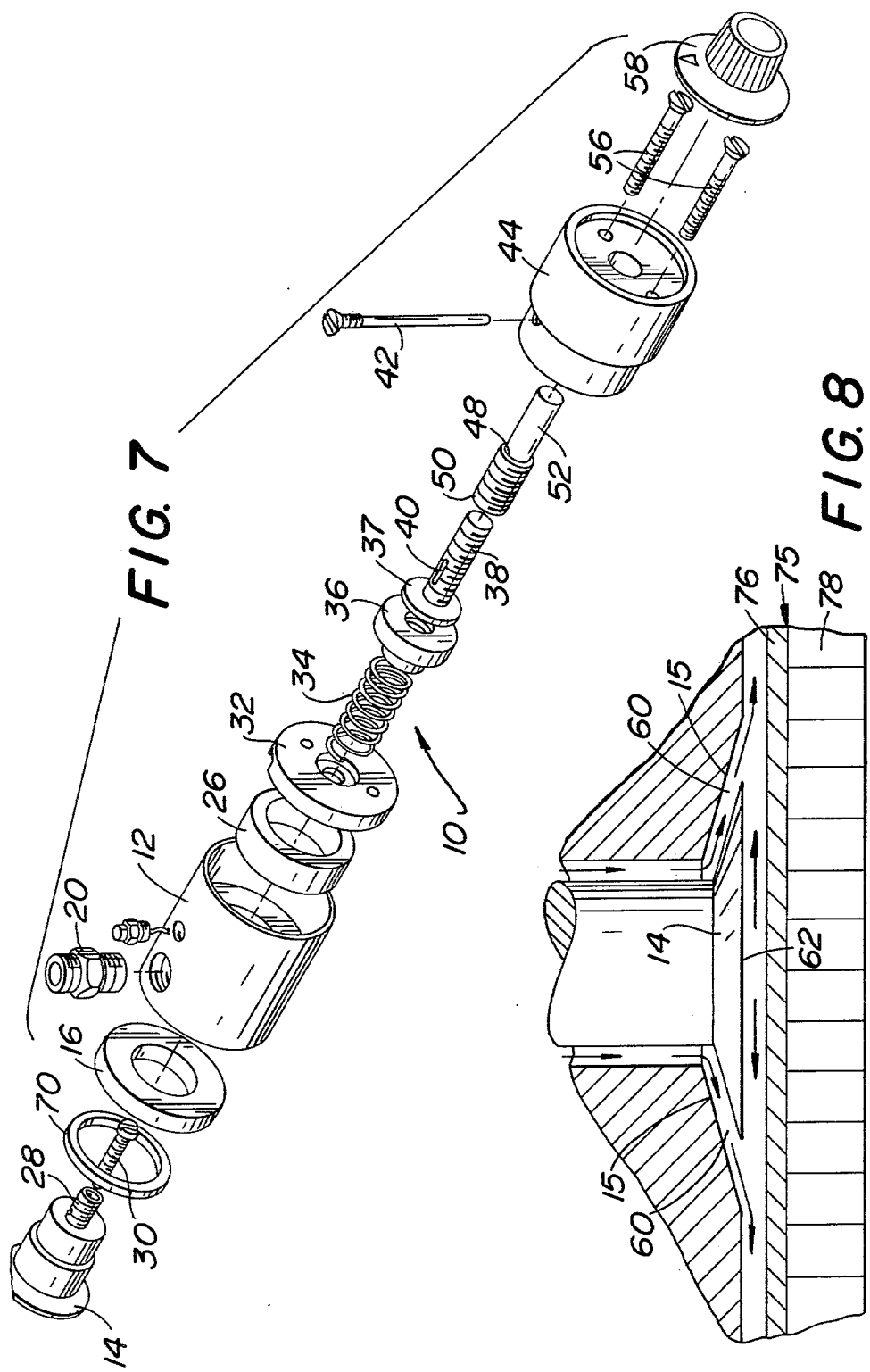

APPARATUS FOR DETECTING BONDING DEFECTS IN LAMINATES

BACKGROUND OF THE INVENTION

Structural panels requiring light weight but high rigidity, notably aircraft wings, may be made of a construction wherein honeycomb or other cellular type material acts as a substrate which is bonded at its upstanding edges to a face sheet. It is important in these structural panels that a secure adhering bond be maintained between the face sheet and the substrate substantially over the entire area of the panel. This invention is related to an apparatus for the non-destructive testing of the bonds between the substrate and the face sheet.

Non-destructive testing of the bonds has been accomplished by other known means, including the means disclosed in my U.S. Pat. No. 4,043,179 in which an internally evacuated transducer is arranged to glide easily over the surface being scanned while maintaining a constant or pulsating vacuum. When the apparatus of my prior patent is drawn over an area where the face sheet is not properly bonded to the substrate, the face sheet is drawn by the vacuum into a detection chamber where detection is accomplished by the displacement of core rods in one or more linear variable differential transformers (LVDT).

As my prior invention was an improvement over an earlier suction-type device, so also is this invention an improvement on my prior apparatus. The present invention takes advantage of the principle of creating an air cushion beneath the apparatus by high velocity air jets, which provides a virtually frictionless bearing surface so that the detection apparatus may be easily and rapidly skimmed over the face sheet. Advantage is taken of the Bernoulli principle of moving fluids in order to use the air jets producing the air cushion to simultaneously produce a vacuum to displace the face sheet in areas where the sheet is not properly bonded to the substrate. Advantage is also taken of the principles of capacitance gauges in order to detect when the substrate is displaced toward the testing apparatus by the vacuum.

It should be apparent at this point, and will become clear upon reading the disclosure, that there are many significant advantages in the present invention. The examining surface of the present apparatus does not come in contact with the face sheet. This eliminates the need for hermetic seals as required by the earliest detection devices of this type, and also removes the necessity of a separate vacuum chamber and counteracting compressed air portion separated by seals, as in my previous apparatus. Considerable weight is eliminated by not having a requirement for separate evacuating means and air compressing means. In addition, the capacitance gauge sensing eliminates considerable weight as compared to the LVDT's and provides sensing of smaller displacements of the face sheet.

These and other advantages will become apparent upon reading the disclosure which follows.

SUMMARY OF THE INVENTION

In accordance with the preferred embodiments, an apparatus is provided for testing of bonded laminates which includes a substrate and a face sheet bonded thereto. The apparatus includes means for producing an air cushion between an examining surface of the apparatus and the face sheet of the laminate by applying high velocity air from at least one air nozzle in the examining surface. A portion of the examining surface is a detection plate having associated therewith means for detecting deflection of the face sheet of the laminate toward the detection plate. Means are provided for producing a vacuum in the area between the detection plate and the face sheet, whereby the face sheet will be deflected toward the detection plate in any area where the face sheet is not bonded to the substrate.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 7 is an exploded view of the testing device of FIG. 1.

FIG. 8 is a partial vertical sectional view of the testing device of FIG. 1 in operating position over a part of a panel being tested.

DETAILED DESCRIPTION OF THE PREFERRED EMBODIMENTS

Figure 1:
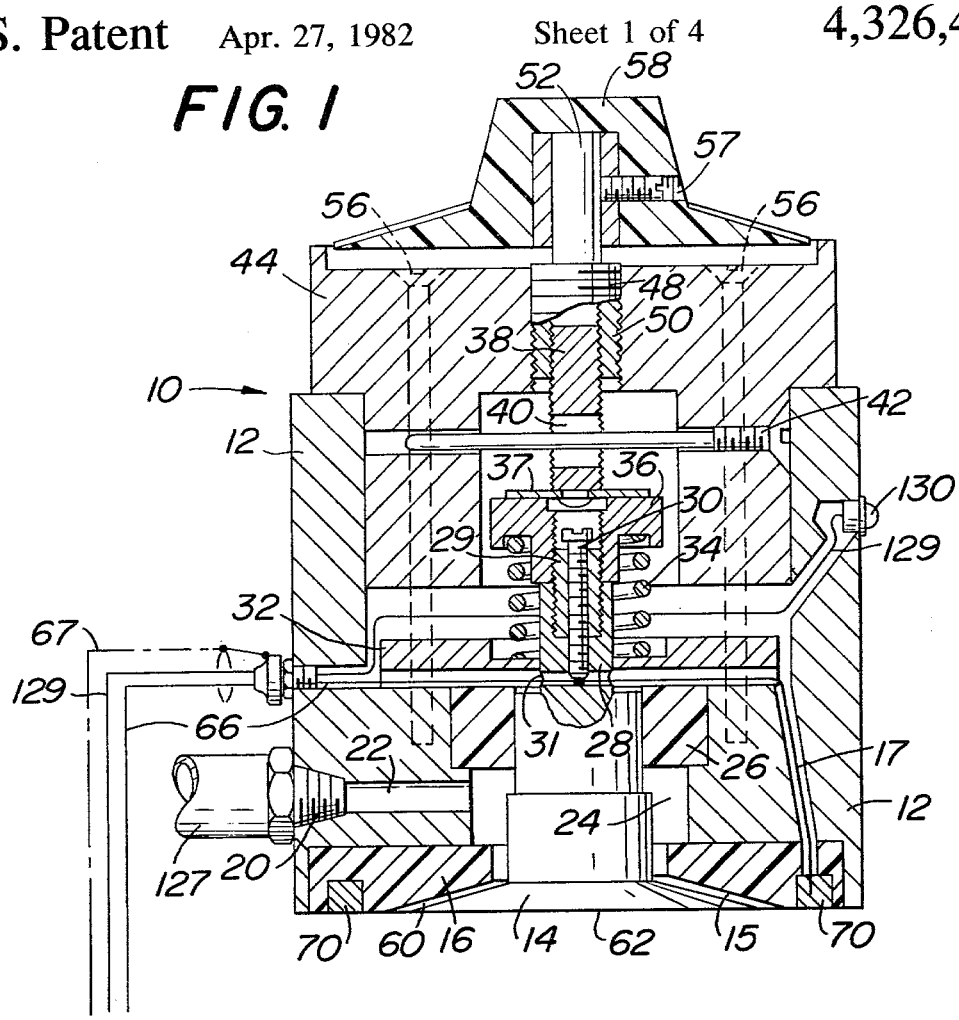
FIG. 1 is a vertical sectional view of the testing device of the present invention.

Referring to the drawings in detail, wherein like numerals indicate like elements, there is shown in FIGS. 1 and 7 a testing device 10 constructed in accordance with the principles of the present invention. Testing device 10 comprises a lower housing 12 and an upper housing 44. Housings 12 and 44 may be generally hollow cylinders constructed to fit together to provide a single body portion.

Recessed in a lower open end of lower housing 12 is a non-metallic ring 16 having a generally conical depression in the middle thereof to form a valve seat 15 for a generally conical valve 14. The sides of the conical portion of valve 14 should have a generally shallow angle, and the valve seat 15 portion of ring 16 should slope at the same angle to make a conformal fit with valve 14. Ring 16 may be constructed of insulating material, such as nylon, while valve 14 should be of metal or other material having strong electrical conduction properties.

A fitting 20 is provided in lower housing 12 through which may be input compressed air passes from an exterior compressed air source. Fitting 20 may preferably be a threaded attachment for a compressed air hose 127. Fitting 20 communicates with an interior air channel 22 in lower housing 12, which in turn communicates with an air manifold 24 surrounding valve 14. An insulating ring 26, preferably of nylon, separates and electrically insulates valve 14 from lower housing 12.

A lug 28 may be machined as an integral part of the upper portion of valve 14. Lug 28 has a threaded bore into which a threaded plug 29 extends. A channel 31 extends through the wall near the base of lug 28. A screw 30 is threaded into bores of plug 29 and lug 28 and clamps in place wires 17 and 66 extending through channel 31. A base ring 32 is placed inside lower housing 12 and around lug 28. Wires 17 and 66 pass through arches 35 in the sides of ring 32. A steel spring 34 is placed over lug 28 and contacts base ring 32. A threaded cap 36 is screwed down on plug 29, and maintains spring 34 in compression.

Upper housing 44 has a threaded channel into which a vertical member 48 is threaded. Member 48 has a hollow cylindrical lower portion 50 which is threaded on both the inside and the outside, and a smaller diameter cylindrical upper portion 52. A threaded lug 38 is screwed into the bore of lower portion 50 of member 48. Threaded lug 38 has a vertical opening 40 which passes entirely through lug 38. Lug 38 is screwed into the threaded bore of member 48 but not so far as to cover the opening 40. A screw 42 passes through apertures in the side of upper housing 44 and through the opening 40 of lug 38.

The upper portion 52 of member 48 extends above upper housing 44. Upper housing 44 is placed inside lower housing 12 to form a generally cylindrical housing and long threaded screws 56 hold the upper and lower housings together. An indicator cap 58 is placed over the upper portion 52 and sits in a circular recess in upper housing 44. A short screw 57 passes through an aperture in cap 58 and contacts upper member 52, thus holding cap 48 in a fixed position on member 52. It may be seen that by rotating indicator cap 58, the valve 14 may be moved into or away from valve seat 15 by the thread movement of member 48 around threaded lug 38. Threaded lug 38 cannot itself rotate because of screw 42. However, threaded lug 38 may move up and down along screw 42 over the limits of vertical opening 40. This movement is translated from lug 38 to valve 14 by washer 37, cap 36, spring 34 and base ring 32.

When high pressure compressed air is introduced through air hose 127 and a fitting 20, the air passes through channel 22 and into air manifold 24, and diffuses out of apparatus 10 through the air gap 60 between valve seat 15 and valve 14. Given a constant pressure air source, the velocity of the air escaping through air gap 60 depends on the dimensions of air gap 60 and thus on the position of valve 14 with respect to the valve seat 15. Air gap 60 thus functions as a nozzle in directing the air out of apparatus 10 and imparting to the air a velocity corresponding to the dimensions of gap 60.

FIG. 8 illustrates the effect of high velocity compressed air being ejected through the nozzle formed by air gap 60. The air is directed at an angle which has a relatively large horizontal component and a relatively small vertical component. When the apparatus is placed above a surface to be examined, shown here as laminate 75 comprising a face sheet 76 and a honeycomb substrate 78, the ejected air forms an air cushion beneath the device 10 radially outwardly of the valve 14. Beneath the valve 14, the Bernoulli effect of the high velocity air creates a vacuum. The term "vacuum" is used herein to denote a lower pressure than atmospheric pressure to create a suction, but not necessarily an absolute vacuum. Thus, two desirable effects are simultaneously created. The air cushion provides a virtually frictionless air bearing by which the device may easily be translated across the surface of the face sheet 76, even though the face sheet 76 may have rivets or other irregularities. Simultaneously, a vacuum is being produced underneath valve 14 whereby if the valve 14 should pass over an area of the laminate in which the face sheet 76 is not properly bonded to the substrate, the face sheet 76 will lift away from the substrate and deflect toward the valve 14.

Thus, the lower surface of the valve 14 acts as a detection plate 62. The entire lower surface of apparatus 10 is referred to herein as an examining surface, but detection of defects is accomplished by the detection plate 62 which is the lower surface of valve 14.

Figure 6:
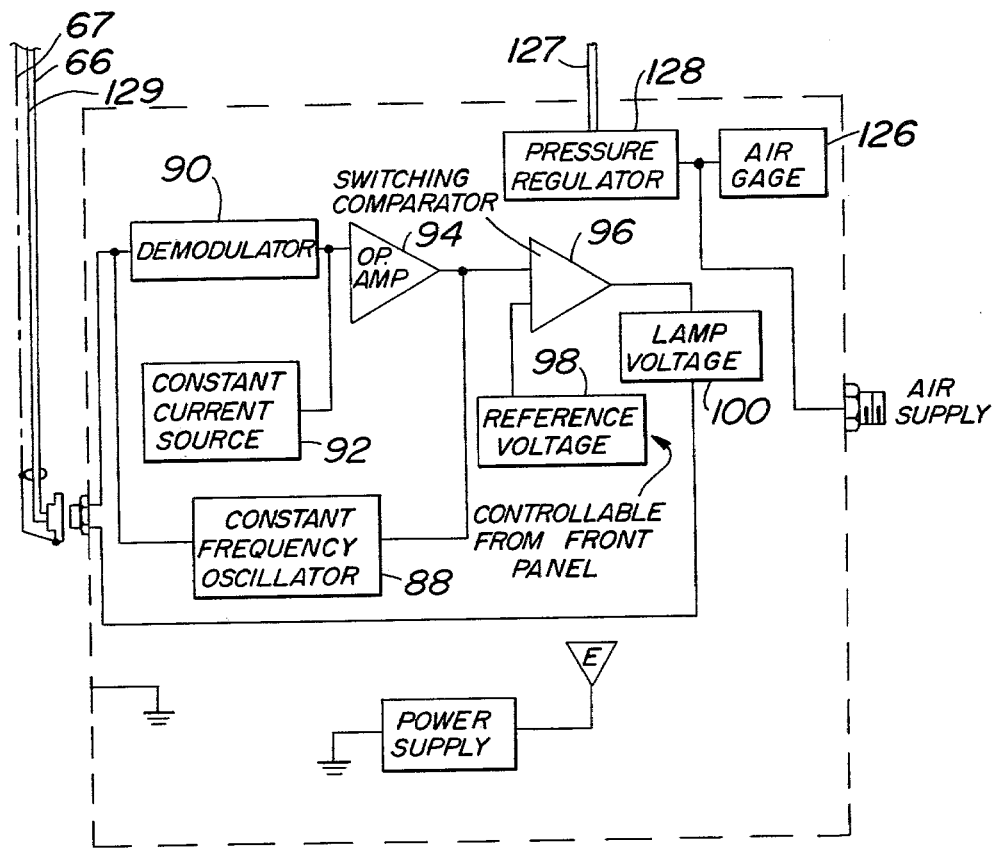
FIG. 6 is a block diagram of a portion of the electrical control circuitry and air control means of the present invention.

Detection is accomplished by the principles of capacitance sensing. An alternating current voltage is supplied to valve 14. The principles of capacitance sensing are known, and reference may be made to the article "Greater Precision For Non-Contact Sensors" published in the Dec. 6, 1979 issue of *Machine Design*, pages 117–121 which is hereby incorporated by reference. Briefly, an alternating voltage is applied to detection plate 62 by a wire 66 from an exterior source. Detector plate 62 thus functions as one plate of a capacitor. In order to eliminate electrostatic interference between detector plate 62 and lower housing 12, a metallic guard ring 70 is embedded in the non-conducting valve seat ring 16, and is maintained at the same electrical potential as detection plate 62 by guard wire 17. A shield wire 67 keeps the housing 12 at ground potential. The lower surface of metallic guard ring 70 lies substantially in a plane with detection plate 62, to ensure that the electrostatic force lines between detection plate 62 and the face sheet 76 are substantially parallel. Face sheet 76 will normally be maintained at ground potential, and thus acts as the second plate of the capacitor. The capacitance of the resulting capacitor formed by the detection plate 62 and the face sheet 76 is dependent on the dielectric properties of the air gap separating the face sheet 76 from the detection plate 62. When the air gap is changed by the face sheet 76 deflecting toward the detection plate 62 under the influence of the vacuum, the reduction in the air gap will show up as an increased capacitance. The increased capacitance may be sensed by the electrical circuitry shown in block diagram form in FIG. 6. A constant frequency oscillator 88 provides high frequency excitation energy for the capacitor. The resulting current across the capacitor will be dependent on the air gap. This current may be converted to a voltage inversely proportional to the air gap by the action of the demodulator 90, the constant current source 92 and operational amplifier 94 (hereinafter op-amp 94). The demodulator 90 converts the AC current signal to a direct current. A constant current source 92 puts out a constant reference current which is connected to the line between demodulator 90 and op-amp 94. Op-amp 94 has its output connected to the constant frequency oscillator 88 and varies the amplitude of the voltage from oscillator 88 in order to maintain a current from demodulator 90 which is equal and opposite the reference current from current source 92. Op-amp 94 controls oscillator 88 by varying the voltage at the output of op-amp 94. Thus, the voltage at the output of op-amp 94 is proportional to the amplitude of the current across the capacitor comprising detector plate 62 and face sheet 76.

Figure 2:
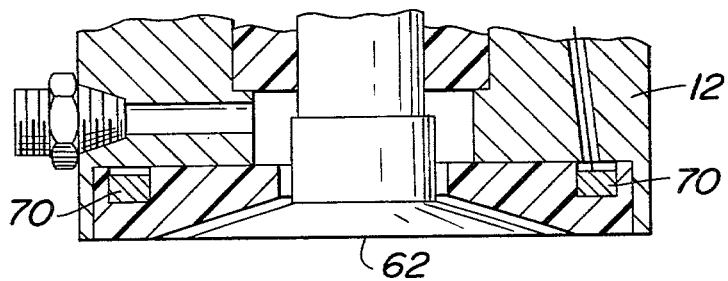
FIG. 2 is a vertical sectional view of a lower portion of an alternative embodiment of the testing device.

Referring now to FIG. 2, an alternative embodiment is shown for use where the face sheet 76 is composed of a non-conducting or dielectric material. In those instances, the face sheet 76 will not serve as a capacitor plate. The capacitor must therefore be between detection plate 62 and the lower extremity of lower housing 12. This distance will not change. However, the dielectric properties of the face sheet 76 will be different from that of air, and consequently movement of the face sheet 76 toward the detection plate will produce a fringing effect on the capacitance. This fringing effect may be measured in a manner similar to the direct capacitance sensing of the previous embodiment. It is necessary to change the position of guard ring 70 in this embodiment. Specifically, guard ring 70 must be recessed to allow lectrostatic field between the detection plate 62 and the lower surface of lower housing 12.

Figure 3:
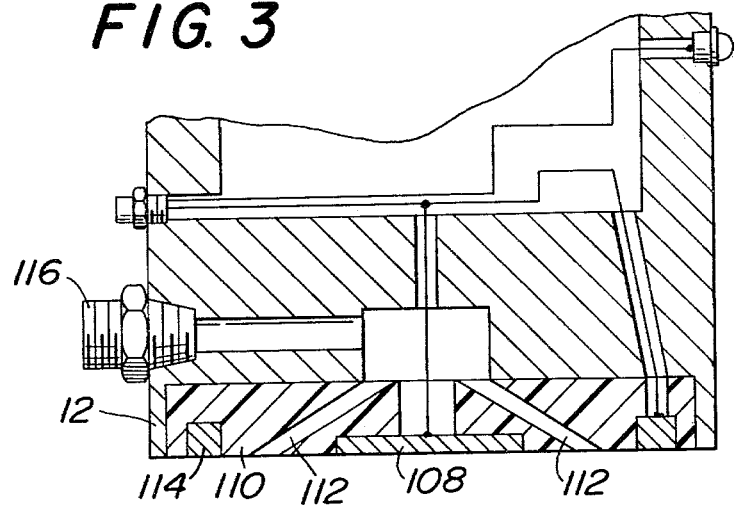
FIG. 3 is a vertical sectional view of a lower portion of an alternative embodiment of the testing device.
Figure 4:
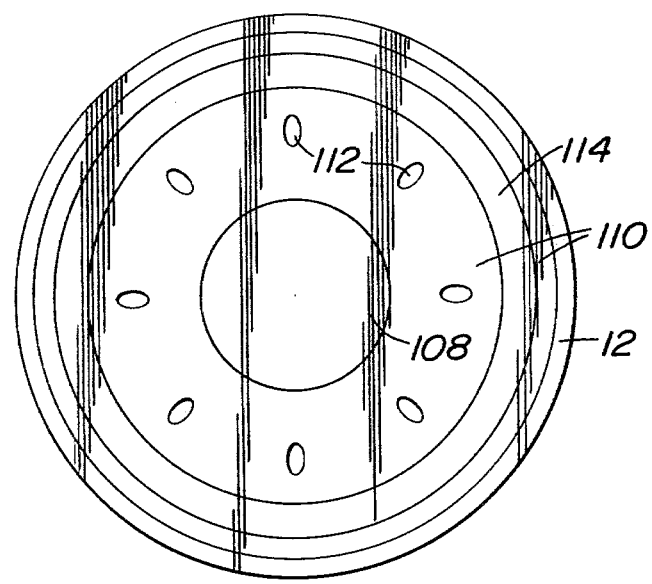
FIG. 4 is a bottom plan view of the testing device of FIG. 3.

A third embodiment is shown in FIG. 3. In FIG. 3, there is no movable valve. Instead, there is simply a metallic detection plate 108 recessed in a non-conductor ring 110. A set of air nozzles 112 are provided in ring 110 in a generally circular pattern, as may be seen in FIG. 4. This embodiment may have the guard ring 114 placed as shown for use with a metallic face sheet, or guard ring 114 may be recessed as in FIG. 2 for use with a non-conducting face sheet.

Otherwise, FIG. 3 works in a mannerr similar to FIGS. 1 or 2, except that the size of the air nozzles cannot be varied. Therefore, the air velocity can only be adjusted by varying the pressure of the air through the fitting 116.

Figure 5:
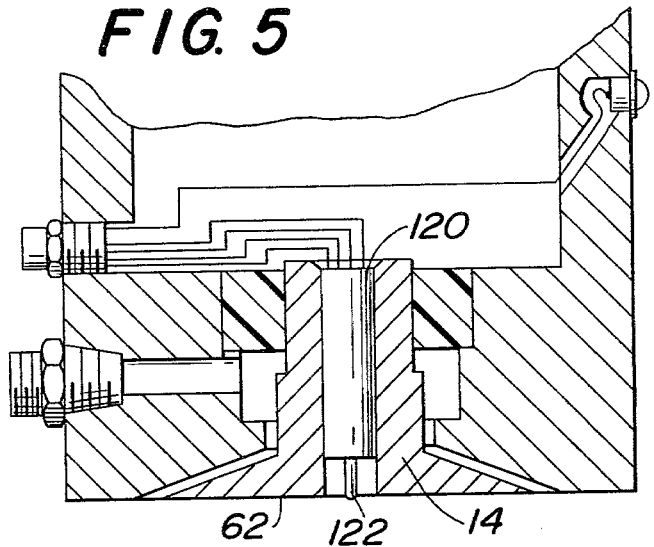
FIG. 5 is a vertical sectional view of a lower portion of an alternative embodiment of the testing device.

The preferred method of detection as outlined above is capacitance sensing. However, the invention is not necessarily restricted to capacitance sensing. A linear variable differential transformer (hereinafter "LVDT") as shown in FIG. 5 may be used, for example. In FIG. 5, LVDT 120 is embedded in valve 14. The core of LVDT 120 extends as a spring-biased probe 122 beyond the detection plate surface 62 of valve 14. If the face sheet in a non-bonded area is pulled by the vacuum toward detection plate 62, it will contact probe 122 and push it deeper inside LVDT 120, thus causing a linear change in the transformer properties. This change may be detected by an appropriate conventional detection circuit.

Another detection technique which may be used is simply viewing an air qauge 126 (shown symbolically in FIG. 7). When using the testing device, including an air gauge, large area defects in the face sheet bonding which result in a substantial deflection of the face sheet 76 cause a back pressure indication which shows up as a pressure rise on the air gauge 126, which is normally used to indicate the pressure being put out by pressure regulator 128. While it is not as accurate in the detection of small scale deflections as capacitance sensing, there may well be applications where only gross defects need be sensed. In those applications, it may be sufficient to provide sensing by monitoring an air gauge only. However, in the preferred embodiment, capacitance sensing is the primary sensor and the air gauge may be monitored as a secondary sensor.

Whatever electrical sensing is used, whether capacitance sensing or LVDT's, a warning light 130 preferably is provided on lower housing 12. This warning light 130 is controlled through wire 129 by the circuitry shown in FIG. 7. The output of op-amp 94 is a voltage signal inversely proportional to the air gap between the capacitance plates. This voltage is input to one terminal of switching comparator 96. The other terminal of switching comparator 96 is set to a fixed reference voltage source 98. Thus, switching comparator 96 will put out a positive voltage signal when the voltage output from op-amp 94 is greater than the reference voltage from reference voltage source 98. This output is sent through an amplifier 100 and is used to illuminate the lamp.

From the foregoing, it may be seen that an apparatus for detecting bonded defects in laminates has been provided which meets all of the objectives set forth above. However, the present invention may be embodied in other specific forms without departing from the spirit or essential attributes thereof, and, accordingly, reference should be made to the appended claims, rather than to the foregoing specification, as indicating the scope of the invention.

I claim:

1. Apparatus for testing bonded laminates which include a substrate and a face sheet bonded thereto, comprising:
   (a) means for producing an air cushion between an examining surface of the apparatus and the face sheet of the laminate by applying high velocity air flow from at least one air nozzle in the examining surface;
   (b) the examining surface including a detection plate having means for detecting deflection of the face sheet of the laminate toward the detection plate; and
   (c) means for producing a vacuum in the area between the detection plate and the face sheet, whereby the face sheet will be deflected toward the detection plate in any area where the face sheet is not bonded to the substrate.

2. Apparatus as in claim 1 wherein the means for producing the air cushion includes at least one air nozzle oriented to direct high velocity air in a direction generally radially outwardly of the plate, and the means for producing the vacuum includes the plate to be spaced from the face sheet by the air cushion with the area beneath the plate being in direct communication with the air cushion.

3. Apparatus as in claim 2 wherein the air nozzle comprises a generally circular channel around the detection plate.

4. Apparatus as in claim 3 further comprising means for regulating the velocity of the air by changing the dimensions of the air nozzle.

5. Apparatus as in claim 4 further comprising a valve having a flat base, the base serving as the detection plate, and the air nozzle is formed by a channel between the valve and a valve seat area.

6. Apparatus as in claim 5 wherein the means for changing the dimensions of the air nozzle comprises means for positioning the valve toward or away from the valve seat whereby the dimensions of the channel between the valve and the valve seat are changed.

7. Apparatus as in claim 1 or 2 wherein the means for detecting deflection of the face sheet of the laminate toward the detection plate includes means for applying an alternating voltage to the detection plate whereby the detection plate becomes one plate of a capacitor and the face sheet of the laminate becomes a second plate of the capacitor, and means for detecting the change in the direction between the plate and the face sheet by the change in current flow to the detection plate.

8. Apparatus as in claim 1 or 2 wherein the face sheet is a non-conducting material and the means for detecting deflection of the face sheet of the laminate toward the detection plate includes means for applying an alternating voltage to the detection plate, whereby the detection plate becomes one plate in a capacitor, and means for insulating the detection plate from a grounded portion of the examining surface the grounded portion acting as a second capacitor plate, and means for detecting the change in distance between the detection plate and the face sheet by the change in current flow to the detection plate.

9. Apparatus as in claim 1 or 2 wherein the means for detecting deflection of the face sheet of the laminate toward the detection plate includes one or more spring biased probes extending through the detection plate, each probe having an upper extremity which is a core of a linear variable differential transformer, the deflection of the face sheet toward the deflection plate being detected by the change in the linear variable transformer properties as the face sheet contacts the probe and pushes the probe deeper into the transformer.

10. Apparatus as in claim 1 or 2 wherein the means for detecting deflection of the face sheet of the laminate toward the detection plate includes an air pressure meter for measuring the static pressure of the air introduced to the nozzles, whereby an increase in the pressure indicated on the pressure gauge indicates that the face sheet has deflected toward the detection plate.

11. Apparatus for testing bonded laminates which include a substrate and a face sheet bonded thereto, comprising:
    (a) at least one air nozzle arranged in a pattern on an examining surface of the apparatus to direct high velocity air in a direction generally radially outwardly of the pattern;
    (b) the examining surface including a detection plate located inwardly of the pattern, the detection plate having associated therewith means for detecting deflection of the face sheet of the laminate toward the detection plate;
    (c) means for introducing high pressure air through the air nozzle thereby producing an air cushion between the examining surface of the apparatus and the face sheet of the laminate and simultaneously producing a vacuum in the area between the detection plate and the face sheet.

12. Apparatus as in claim 11 wherein the air nozzle comprises a generally circular channel around the detection plate.

13. Apparatus as in claim 12 further comprising a conical valve having a flat base, the base serving as the detection plate, and a channel between the sides of the valve and a recessed valve seat.

14. Apparatus as in claim 13 further comprising means for regulating the velocity of the air by changing the dimensions of the air nozzle.

15. Apparatus as in claim 14 wherein the means for changing the dimensions of the air nozzle comprises means for positioning the conical valve toward or away from the valve seat whereby the dimensions of the channel between the sides of the valve and the valve seat are changed.

16. Apparatus as in claim 11 or 15 wherein the means for detecting deflection of the face sheet of the laminate toward the detection plate includes means for applying an alternating voltage to the detection plate whereby the detection plate becomes one plate of a capacitor and the face sheet of the laminate becomes a second plate of the capacitor, and means for detecting the change in the distance between the plate by the change in current flow to the detection plate.

17. Apparatus as claim 11 or 15 wherein the face sheet is a non-conducting material and the means for detecting deflection of the face sheet of the laminate toward the detection plate includes means for charging the detection plate with an alternating voltage whereby the plate becomes one plate in a capacitor and means for insulating the detection plate from a grounded portion of the examining surface, the grounded portion acting as a second plate of the capacitor, and means for detecting the change in distance between the detection plate and the face sheet by the change in current to the detection plate.

* * * * *